US012758345B2

(12) United States Patent
Novak et al.

(10) Patent No.: US 12,758,345 B2
(45) Date of Patent: Oct. 13, 2026

(54) MEDICAL CONTAINER PACKAGING

(71) Applicants: Wenzel Novak, Bünde (DE); Ramses Cuevas, Deptford, NJ (US); Udo Leuschner, Regensburg (DE); Riccardo Prete, Ponte San Nicolo (IT)

(72) Inventors: Wenzel Novak, Bünde (DE); Ramses Cuevas, Deptford, NJ (US); Udo Leuschner, Regensburg (DE); Riccardo Prete, Ponte San Nicolo (IT)

(73) Assignees: Gerrersheimer Glas GmbH, Düseldof (DE); Stevanato Group S.p.A., Piombino Desse (IT)

( * ) Notice: Subject to any disclaimer, the term of this patent is extended or adjusted under 35 U.S.C. 154(b) by 0 days.

(21) Appl. No.: 18/351,995

(22) Filed: Jul. 13, 2023

(65) Prior Publication Data

US 2024/0016569 A1 Jan. 18, 2024

Related U.S. Application Data

(60) Provisional application No. 63/390,153, filed on Jul. 18, 2022.

(51) Int. Cl.
*A61B 50/30* (2016.01)

(52) U.S. Cl.
CPC ...... *A61B 50/30* (2016.02); *A61B 2050/3014* (2016.02)

(58) Field of Classification Search
CPC ........................ A61B 50/30; A61B 2050/3014
USPC .................................................. 206/438, 366
See application file for complete search history.

(56) References Cited

U.S. PATENT DOCUMENTS

| | | | | |
|---|---|---|---|---|
| 4,752,453 A | | 6/1988 | Nichols | |
| 4,798,292 A | | 1/1989 | Hauze | |
| 5,346,075 A | * | 9/1994 | Nichols | A61B 50/31 206/363 |
| 5,353,930 A | * | 10/1994 | Berry, Jr. | B29C 51/14 206/439 |
| 5,372,787 A | | 12/1994 | Ritter | |
| 5,490,975 A | * | 2/1996 | Dane | A61L 2/26 206/439 |
| 5,518,115 A | * | 5/1996 | Latulippe | B65D 25/10 206/370 |
| 5,590,778 A | | 1/1997 | Dutchik | |

(Continued)

FOREIGN PATENT DOCUMENTS

| | | |
|---|---|---|
| CN | 101652152 A | 2/2010 |
| CN | 103298504 A | 9/2013 |

(Continued)

OTHER PUBLICATIONS

Extended European Search Report in European Appln. No. 22188946.2, dated Dec. 22, 2022, 8 pages.

(Continued)

*Primary Examiner* — Jacob K Ackun
(74) *Attorney, Agent, or Firm* — Fish & Richardson P.C.

(57) ABSTRACT

A tub includes a bottom wall and sidewalls extending from the bottom wall. The sidewalls form an opening at a top of the tub opposite to the bottom wall. The bottom wall includes one or more apertures through the bottom wall. A porous fiber material can be disposed over the one or more apertures of the bottom wall.

18 Claims, 8 Drawing Sheets

(56) References Cited

U.S. PATENT DOCUMENTS

| | | | | |
|---|---|---|---|---|
| 5,725,097 | A * | 3/1998 | Bettenhausen | A61L 2/26 292/210 |
| 5,913,422 | A * | 6/1999 | Cote | A61L 2/26 206/370 |
| 6,007,854 | A * | 12/1999 | Cadiente | B65D 5/4295 426/106 |
| 6,164,044 | A * | 12/2000 | Porfano | A61M 5/344 53/489 |
| 6,357,594 | B1 | 3/2002 | Gutentag | |
| 7,521,021 | B2 * | 4/2009 | McCormick | G01N 1/36 422/63 |
| 8,267,246 | B2 * | 9/2012 | Bettenhausen | A61B 50/30 206/439 |
| 8,667,890 | B2 * | 3/2014 | Macchi | B65D 85/8061 426/77 |
| 8,679,404 | B2 | 3/2014 | Liburd et al. | |
| 10,543,054 | B2 | 1/2020 | Houde et al. | |
| 11,000,643 | B2 | 5/2021 | Peruzzo | |
| 11,338,051 | B2 | 5/2022 | Lin et al. | |
| 11,673,709 | B2 * | 6/2023 | Turner | B65D 19/06 206/599 |
| 11,737,849 | B2 * | 8/2023 | Zille | A61B 50/33 206/363 |
| 11,780,639 | B2 * | 10/2023 | Rodriguez | B65D 33/1616 206/423 |
| 2003/0052133 | A1 * | 3/2003 | Hayes | B65D 43/162 206/508 |
| 2004/0222116 | A1 | 11/2004 | Bauer | |
| 2008/0116098 | A1 | 5/2008 | Marooflan et al. | |
| 2008/0131629 | A1 | 6/2008 | Chisholm et al. | |
| 2010/0102057 | A1 * | 4/2010 | Long | A45C 5/02 206/503 |
| 2011/0068019 | A1 | 3/2011 | Jensen et al. | |
| 2011/0071572 | A1 * | 3/2011 | Sixto | A61B 17/8014 606/286 |
| 2013/0108522 | A1 * | 5/2013 | Cohen | B01L 9/543 422/552 |
| 2013/0319888 | A1 * | 12/2013 | Birkbeck | A61B 50/30 206/370 |
| 2013/0341849 | A1 * | 12/2013 | Shimazaki | F26B 5/06 269/287 |
| 2014/0083881 | A1 * | 3/2014 | Oberacker | A01K 97/06 206/315.11 |
| 2014/0209121 | A1 * | 7/2014 | Kamen | B08B 3/047 206/6.1 |
| 2014/0216966 | A1 * | 8/2014 | Ramkhelawan | A61B 50/30 206/370 |
| 2016/0304238 | A1 | 10/2016 | Deutschle et al. | |
| 2018/0207308 | A1 | 7/2018 | Okihara | |
| 2019/0070357 | A1 * | 3/2019 | Evans | A61M 5/008 |
| 2021/0016950 | A1 | 1/2021 | Yoshida | |
| 2022/0371807 | A1 | 11/2022 | Hutterer et al. | |
| 2023/0227243 | A1 * | 7/2023 | Baldwin | B65D 43/162 206/521.1 |
| 2023/0234210 | A1 * | 7/2023 | Heath, Jr. | B25H 3/003 211/70.6 |
| 2024/0016570 | A1 | 1/2024 | Novak et al. | |

FOREIGN PATENT DOCUMENTS

| | | | |
|---|---|---|---|
| CN | 107530489 | A | 1/2018 |
| CN | 213084267 | U | 4/2021 |
| EP | 0513614 | A1 | 11/1992 |
| EP | 2476448 | | 7/2012 |
| JP | S56-156751 | | 11/1981 |
| JP | A-S59-199463 | | 11/1984 |
| JP | U-H3-66870 | | 6/1991 |
| JP | U-H4-114345 | | 10/1992 |
| JP | 2012-071046 | | 4/2012 |
| JP | 5714284 | B2 | 5/2015 |
| TW | 201617275 | | 5/2016 |
| TW | 202132178 | | 9/2021 |
| WO | WO 2015/076780 | | 5/2015 |

OTHER PUBLICATIONS

Office Action in Canadian Appln. No. 3206526, mailed on Dec. 23, 2024, 5 pages.

JP Office Action in Japanese Appln. No. 2023-116170, dated Sep. 10, 2024, 6 pages (with English translation).

JP Office Action in Japanese Appln. No. 2023-116170, dated May 21, 2024, 11 pages (with English translation).

TW Office Action in Taiwanese Appln. No. 112126585, dated Mar. 21, 2024, 15 pages (with English translation).

Office Action in Chinese Appln. No. 202310871832.X, mailed on Jul. 18, 2025, 15 pages (with English Translation).

Office Action in Korean Appln. No. 10-2023-0092495, mailed on May 1, 2025, 16 pages (with English Translation).

* cited by examiner

MEDICAL CONTAINER PACKAGING

CROSS-REFERENCE TO RELATED APPLICATION

This application claims the benefit of U.S. Provisional Application No. 63/390,153, filed Jul. 18, 2022, which is incorporated herein by reference in its entirety.

TECHNICAL FIELD

This disclosure relates to tubs and packaging for sterilized medical containers, such as vials, syringes, and cartridges.

BACKGROUND

Packaging for medical containers are used for sterilization and safeguarded handling and transportation of the medical containers, such as syringes, vials, or cartridges. Sterilization of the contents of the packaging occurs through the injection of a disinfectant through a gas-porous and liquid-resistant material layer covering an entire top opening of a container, or tub, of the packaging. The packaging can be transported from one site to another, such as when it is manufactured at a first location and filled at a second location, or when it is manufactured and filled in the same location and then delivered to another location.

SUMMARY

This disclosure describes a tub for medical container packaging.

In some aspects of the disclosure, a tub comprises a bottom wall comprising at least one aperture through the bottom wall, and a plurality of sidewalls extending from the bottom wall, the plurality sidewalls forming an opening at a top of the tub opposite to the bottom wall.

This, and other aspects, can include one or more of the following features. The bottom wall is substantially rectangular, and the plurality of sidewalls comprises a first set of sidewalls along longitudinal edges of the bottom wall and a second set of sidewalls along lateral edges of the bottom wall. The opening comprises a peripheral flange along top edges of the plurality of sidewalls, the peripheral flange being continuous along the plurality of sidewalls. The at least one aperture comprises a plurality of apertures through the bottom wall. The plurality of apertures are disposed in a symmetrical pattern across a lateral centerline of the bottom wall. The plurality of apertures comprises a first plurality of apertures disposed at a first longitudinal end of the bottom wall and a second plurality of apertures disposed at a second longitudinal end of the bottom wall opposite to the first longitudinal end. The first plurality of apertures comprises a first set of three apertures aligned adjacent to the first longitudinal end of the bottom wall, and the second plurality of apertures comprises a second set of three apertures aligned adjacent to the second longitudinal end of the bottom wall. The tub further comprises a porous fiber material disposed over the at least one aperture of the bottom wall of the tub. The porous fiber material is disposed over the plurality of apertures in strips of porous material. A first strip of the porous material is disposed over the first plurality of apertures, and a second strip of the porous material is disposed over the second plurality of apertures. The porous material comprises Tyvek. The tub is laterally symmetrical and longitudinally symmetrical.

Certain aspects of the disclosure encompass a method of forming a tub for medical containers. The method comprises forming a tub comprising a bottom wall and a plurality of sidewalls extending from the bottom wall, the plurality of sidewalls forming an opening at a top of the tub opposite to the bottom wall, forming at least one aperture in the bottom wall of tub, and sealing the at least one aperture with a porous material.

This, and other aspects, can include one or more of the following features. Sealing the at least one aperture with the porous material comprises overmolding the porous material with the tub or heat sealing the porous material to the tub. Forming the at least one aperture comprises molding the bottom wall of the tub to include the apertures or cutting out the apertures in the bottom wall of the tub. Sealing the at least one aperture comprises sealing with Tyvek. Forming the tub comprises thermoforming or injection molding the tub.

The details of one or more implementations of the subject matter described in this disclosure are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

Figure 1:
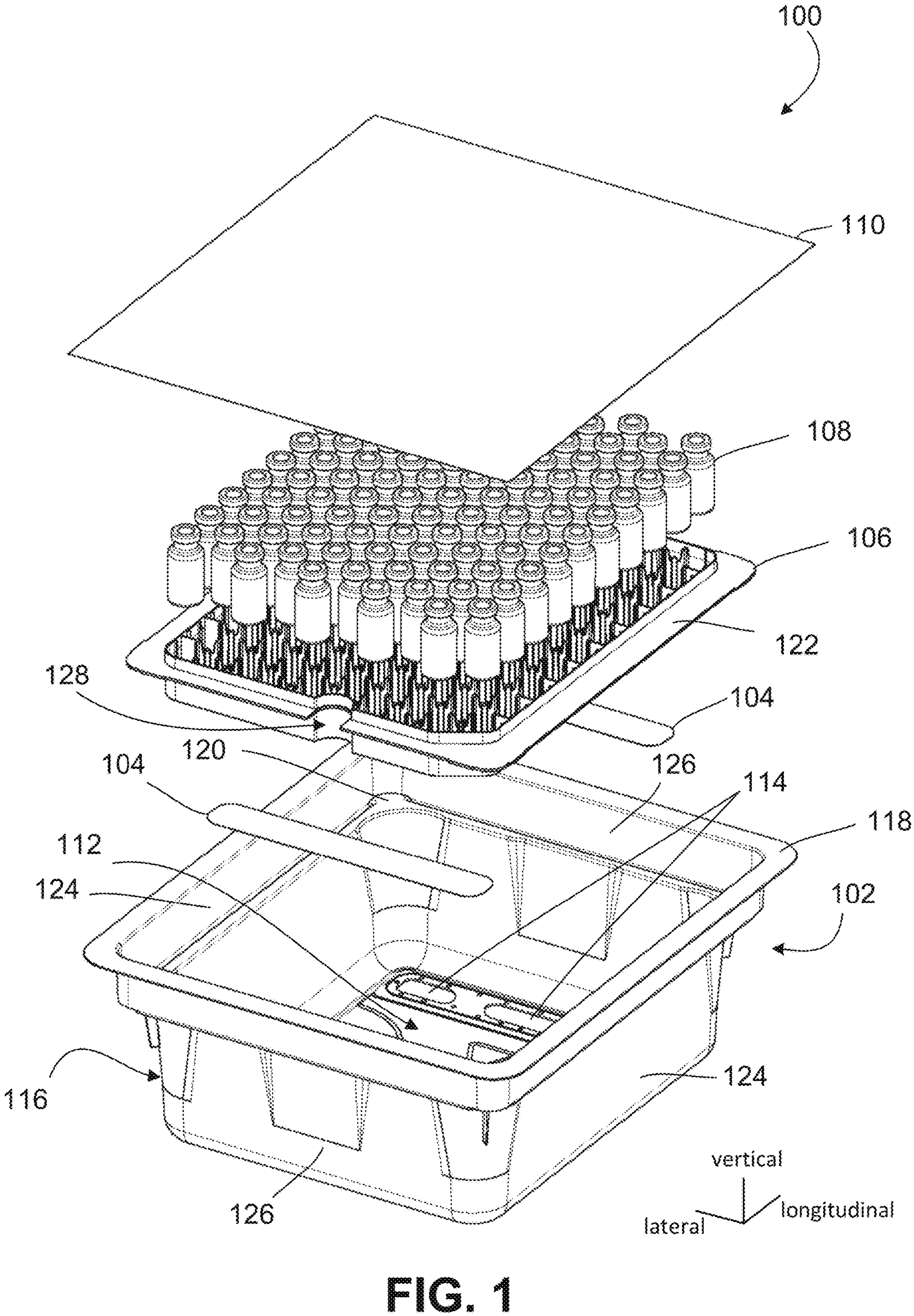
FIG. 1 is an exploded perspective view of an example packaging for medical containers.

This disclosure regards packaging for medical products, such as syringes, vials, cartridges, or other containers. It is important in the medical community to have medical products that are sterile and easily transportable, and medical packaging provides for handling and transportability of sterilized and fragile (e.g., glass) products. In the present disclosure, a packaging for medical products includes a tub with one or more apertures in a bottom wall of the tub, where the apertures are covered and sealed by a porous material, such as a porous fiber material that is gas-porous and liquid-impervious and acts as a selective filter layer over the apertures. The porous material can be overmolded with the tub, heat sealed to the tub, or otherwise connected to the tub to seal the one or more apertures. The apertures and porous material allows for an injection of sterilization gas via the bottom of the tub through the apertures and porous material, for example, to disinfect and sterilize the internal contents of the packaging. The seal of the porous material over the apertures ensures there is no bacterial infiltration and liquid infiltration into the interior space of the tub through the apertures, while still allowing for the injection of disinfectant gas through the porous material. The packaging can also be sealed at a top opening of the tub, such as with an impermeable polymer film, to enclose an interior of the packaging in preparation for transportation, storage, or both.

In some conventional packaging assemblies, the tub has continuous sidewalls and bottom wall that excludes apertures, and a sealing layer disposed over the entire top opening of the tub includes the porous filter material. Removing (e.g., peeling) the sealing layer with the porous material from the top opening can be difficult and often results in substantial particle generation, which can infect or otherwise taint the sterilized contents of the packaging. In the present disclosure, the porous material is relocated to cover one or more apertures in the main body of the tub, such as apertures in the bottom wall, sidewalls, or both. This relocation of porous material reduces an amount of porous material used in the overall packaging, thereby reducing cost, since the amount of porous material used to over the one or more openings is significantly less than a sheet of porous material that covers an entire top opening of the tub. For example, an amount of porous material or semi-permeable material covering the apertures can be between 1% and 100% of the area defining the top opening, such as between 5% and 80%. In some examples, the amount of porous or semi-permeable material covering the apertures is about 15%, 20%, 25%, 30%, or 35% of the area defining the top opening. In certain implementations, the amount of the porous, semi-permeable material is defined according to a sterilization cycle of the packaging. Also, the packaging of the present disclosure incorporates a sealing layer to seal the opening. The sealing layer can exclude porous material, allowing for a faster and/or easier application (e.g., adhesive attachment) of the sealing layer and/or removal (e.g. peeling) of the sealing layer from the tub.

FIG. 1 is an exploded perspective view of an example packaging 100 for medical containers. The example packaging 100 includes a tub 102, an insert 104 of porous, semi-permeable material (two inserts shown) connected to the tub 102, a nest 106 supporting medical containers 108 (e.g., glass vials shown in FIG. 1), and a sealing layer 110 over the tub 102 to enclose the contents within an interior space of the tub 102. The tub 102 includes a bottom wall 112 with at least one aperture 114 (e.g., six total apertures 114 in the example packaging 100, two shown in FIG. 1), peripheral sidewalls 116 extending from a periphery of the bottom wall 112, and a peripheral flange 118 along top edges of the peripheral sidewalls 116. The sidewalls 116 and flange 118 form an opening at a top of the tub 102 opposite to the bottom wall. The opening is large enough to allow the insertion of the nest 106 and its supported containers 108 into the interior space of the tub 102. The porous material inserts 104 are disposed over and cover the apertures 114, and are connected to the tub 102 by overmolding, heat sealing, or other forms of attachment, described in greater detail below.

The tub 102 can be integrally formed from a single material or multiple materials. In some instances, the tub 102 is formed from a molded plastic or thermoformed plastic, such as polystyrene. The tub 102 holds the insert(s) 104 of porous material in place on the tub 102, and in some examples, the inserts 104 of porous material are overmolded with the tub 102 during molding or heat sealed to the tub 102 after formation of the tub 102. The tub 102 is rigid and provides structure and rigidity to the example packaging 100, and provides a substantially enclosed environment for sterilization of contents within the interior space of the tub 102. The material of the tub 102 and the insert 104 of porous material is puncture-resistant, for example, to resist puncture of the tub 102 by a sharp medical container, such as a syringe. Other than the top opening (which can be covered by the sealing layer 110) and the apertures 114 (which are sealed by the insert 104 of porous material), the tub 102 is impervious to fluid penetration.

In the example packaging 100 of FIG. 1, the longitudinal, lateral, and vertical directions are shown in a 3-coordinate axis system. Generally, the longitudinal direction is along the longer dimension of the tub, the lateral direction is along the shorter dimension of the tub, and the vertical direction is along the height dimension of the tub. In some examples, a lateral centerline of the tub is parallel to the lateral dimension and generally bisects the longitudinal side of the tub, and a longitudinal centerline of the tub is parallel to the longitudinal dimension and generally bisects the lateral side of the tub.

The tub 102 can take on a variety of shapes and sizes. In the example packaging 100 of FIG. 1, the sidewalls 116 are substantially tubular and extend vertically from a rectangular periphery of the bottom wall 112. The peripheral flange 118 has a rectangular shape with a substantially flat top surface, and resides at a vertical top of the sidewalls 116. The peripheral flange 118 is integrally formed with the sidewalls 116. Alternatively, the peripheral flange can be otherwise coupled to the sidewalls 116. The sidewalls 116 of the example packaging 100 include a first set of opposing sidewalls 124 along longitudinal edges of the bottom wall 112 and a second set of opposing sidewalls 126 along the lateral edges of the bottom wall 112. In some implementations, the peripheral sidewalls 116 includes an inner shoulder 120 along the entirety or a portion of the continuous length of the sidewalls 116. The shoulder 120 is formed by an outward step in the substantially vertical sidewalls 116, creating a shoulder surface in the interior space of the tub 102. The outward step in the sidewalls 116 also creates a bottom-facing shoulder surface on an exterior of the tub 102, which can be used as a gripping surface for a user or machinery handling the tub 102. The shoulder 120 has a constant vertical height along the sidewalls 116. In the example packaging 100 of FIG. 1, the shoulder 120 spans the entire continuous length of the sidewalls 116 at an intermediate height of the sidewalls 116. The shoulder 120 supports a flanged edge 122 of the nest 106 such that, in an assembled position of the example packaging 100, the flanged edge 122 of the nest 106 rests on the shoulder 120 and the containers 108 are suspended within the interior space of the tub 102.

In the assembled position of the example packaging 100, the nest 106 resides in the interior space of the tub 102 and is suspended above the insert 104 of porous material and the bottom wall 112 of the tub 102. The insert 104 of porous material is sealed to the bottom wall 112 of the tub 102 over the at least one aperture 114, and the porous material is configured to seal the at least one aperture 114 from liquid penetration. The porous material is connected to the tub 102 between the nest 106 and the bottom wall 112 of the tub 102. The sealing layer 110 connects to the peripheral flange 118 to seal the opening at the top of the tub 102. The sealing layer 110 can be adhered, heat sealed, or otherwise sealingly coupled to the peripheral flange 118 to create a hermetic seal between the interior space of the tub 102 and an exterior space of the tub 102. The sealing layer 110 can take a variety of forms. For example, the sealing layer 110 can be a polymer film, such as a clear polyethyne (PE) film or polyethylene terephthalate (PET) film, or a film made from another polymer. The sealing layer 110 can be transparent, for example, to see the contents of the packaging 100 after application of the sealing layer 110. In some implementations, the sealing layer 110 does not need to include porous material in order to allow for sterilization of the contents of the packaging because the porous material inserts 104 are located at the bottom wall 112 of the tub 102. Because the sealing layer 110 does not include porous material, the transparency of the sealing layer 110 allows for visibility of the contents of the packaging 100. For example, a user may be able to inspect the type of contents (for example, vials, syringes, and/or cartridges), size and state of contents (container size, the number of containers within packaging 100, and/or if any containers are broken), and/or other visual and cosmetic details of the contents of the example packaging 100 without requiring a removal of the sealing layer 110 from the example packaging 100. This visual inspection can be beneficial for viewing the contents of the packaging without sacrificing the hermetic seal of the sealing layer 110 to the tub 102 or the sterility of the medical containers in the packaging 100.

In some examples, the tub 102 is made from polystyrene, the insert 104 of porous material is made from a medical grade high-density polyethylene (HDPE), the nest is made from polypropylene, and the sealing layer 110 is made from clear PET-PE.

Figure 2:
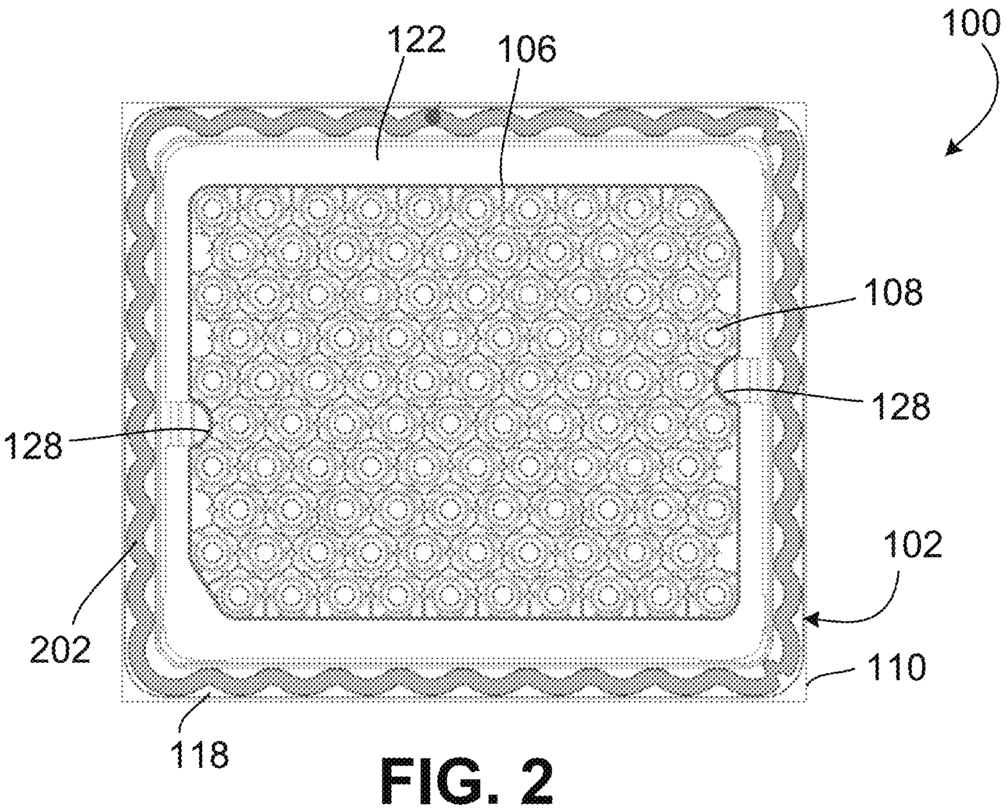
FIG. 2 is a schematic top view of the example packaging of FIG. 1 in an assembled position.

FIG. 2 is a schematic top view of the example packaging 100 of FIG. 1 in the assembled position. The sealing layer 110 is transparent, and the nest 106 and medical containers 108 are visible through the sealing layer 110. The nest 106 securely holds the medical container 108 such that the medical containers 108 are not in direct contact with each other. For example, the medical containers 108 may be glass containers, and the nest 106 holds the glass containers to avoid direct glass-to-glass contact.

In some implementations, the nest 106 includes a recess in a periphery of the nest 106 to allow, for example, to allow disinfectant gas flow from below the nest 106 to above the nest. The recess 128 is formed in the flanged edge 122 of the nest 106, and is formed as an inset in the flanged edge 122. For example, each longitudinal end of the flanged edge 122 of the example packaging 100 of FIG. 2 includes one recess 128 that fluidly connects the interior space of the tub 102 below the nest 106 with the interior space of the tub 102 above the nest 106. The shape and location of the recesses 128 can vary. In the example packaging 100 of FIG. 2, the recesses 128 are semicircular in shape, and align with an existing gap of the medical containers 108 in the nest 106. For example, the medical containers 108 are disposed in the nest 106 in an offset row-by-row pattern to maximize the number of containers 108 that can fit on the nest 106, and the recesses 128 align with existing gaps in the periphery of the offset pattern of the medical containers 108 so as not to detract from the number of containers 108 that fit on the nest 106. In certain implementations, the recesses 128 can be used as finger holds or hand holds during the filling and/or removal of the nest 106 from the tub 102 by a user or machine.

In some implementations, the sealing layer 110 connects to the peripheral flange 118 with adhesive 202 between the peripheral flange 118 and the sealing layer 110. In the example packaging 100 of FIG. 2, the adhesive 202 is disposed in a continuous, non-linear pattern along the peripheral flange 118, such as in a sinusoidal pattern of the adhesive 202 along the peripheral flange 118. The pattern of adhesive 202 is continuous to preserve a complete seal around the peripheral flange 118, and the continuous, non-linear pattern of the adhesive 202 provides for an easier peeling of the sealing layer 110 from the peripheral flange 118 as compared to a linear pattern of adhesive along the peripheral flange 118. For example, the non-linear pattern avoids a high breakout peel force required in instances where the sealing layer 110 is peeled away from a complete line of adhesive at one time. In other words, the non-linear pattern of adhesive 202 requires a lower magnitude of peel force at any given point during peeling compared to a peel force required to unpeel an entire straight line of adhesive at one time. In certain implementations, the pattern of the adhesive 202 along the peripheral flange 118 reduces the peeling force required when peeling off foils of the top sealing layer 110 due to the geometric shape of the adhesive 202 pattern. For example, an introduction of peeling force can be reduced to geometrically defined areas. The pattern of adhesive 202 can take a variety of forms, such as a zig-zag pattern, sinusoidal pattern, wave pattern, curved pattern, wave-like pattern, or other continuous pattern.

The sealing layer 110 can be removed in a variety of ways, for example, in order to perform a filling operation of the medical containers 108. In some examples, the sealing layer 110 is removed by manually peeling the sealing layer 110 from the peripheral flange 118, such as by manual stripping of the sealing layer 110. In certain examples, the sealing layer 110 is removed by suction roller cutting or grating, such as by a machine.

Figure 3:
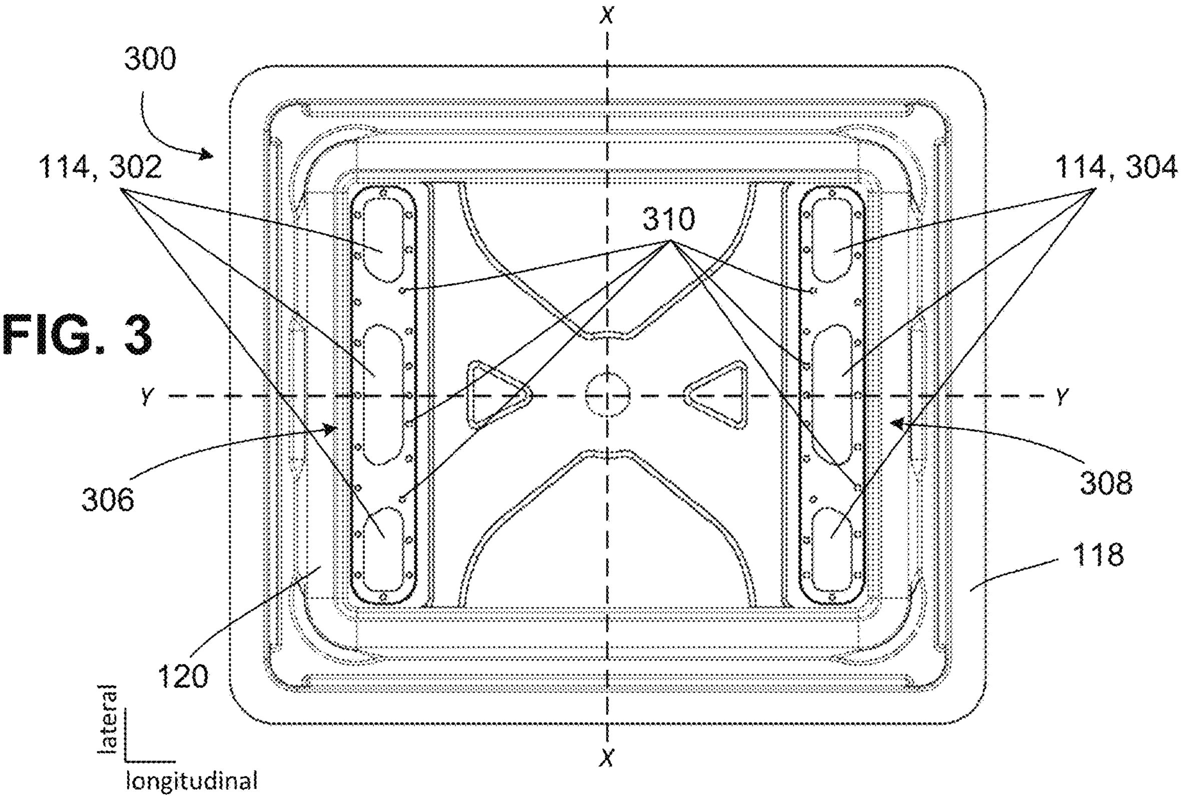
FIG. 3 is a schematic bottom view of an example tub that can be used in the example packaging of FIG. 1.
Figure 5:
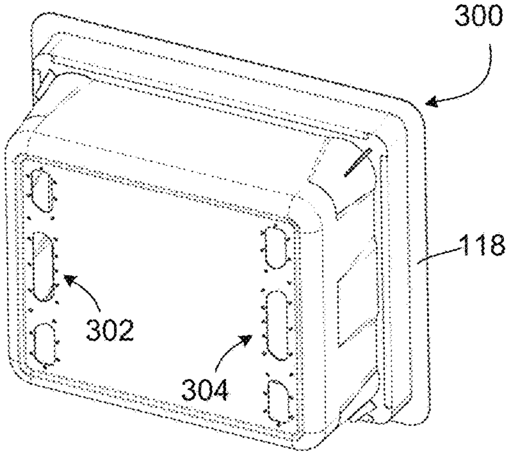
FIGS. 5, 6, and 7 are a schematic bottom perspective view, schematic top perspective view, and schematic bottom view, respectively, of the example tub of FIG. 3.
Figure 6:
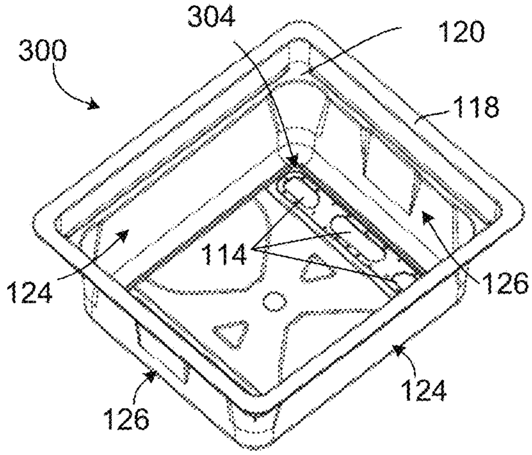
Figure 7:
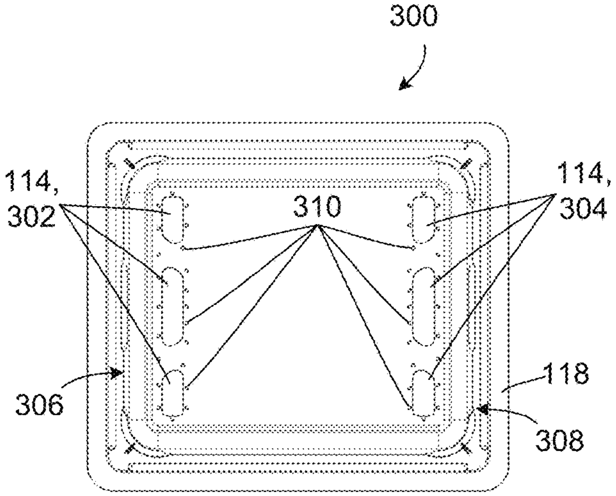

FIG. 3 is a schematic bottom view of an example tub 300. The example tub 300 of FIG. 3 is the same as the example tub 102 of FIG. 1, and can be used in the example packaging 100 of FIG. 1. FIGS. 5, 6, and 7 are a schematic bottom perspective view, schematic top perspective view, and schematic bottom view, respectively, of the example tub 300 of FIG. 3. The example tub 300 includes a plurality of apertures 114 through the bottom wall 112 of the tub 300. The apertures 114 are disposed in the bottom wall 112 in a symmetrical pattern. In some instances, the entire tub 300 including the apertures 114 is symmetrical across a lateral centerline X-X, across a longitudinal centerline Y-Y, or both. The symmetry of the example tub 300 and apertures 114 can allows for flexibility in the orientation of the tub 300, such as during manufacturing, filling, and/or transportation of the tub 300. For example, the symmetry of the tub 300 can be beneficial for medical container assemblers and pharmaceutical customers in that the example tub 300 can be oriented in either direction while still allowing for the same operational steps, such as sterilization, assembly, and/or storage.

The apertures 114 of the example tub 300 of FIGS. 3 and 5-7 include a first plurality of apertures 302 disposed at a first longitudinal end 306 of the bottom wall 112, and include a second plurality of apertures 304 at a second longitudinal end 308 of the bottom wall 112 opposite to the first longitudinal end 306. The first plurality of apertures 302 are symmetrical with the second plurality of apertures 302 across the lateral centerline X-X, and across the longitudinal centerline Y-Y. The first plurality of apertures 302 and the second plurality of apertures 304 each include three total apertures. However, the number, size, and shape of the apertures can vary. For example, each plurality can include more or fewer apertures.

Figure 8:
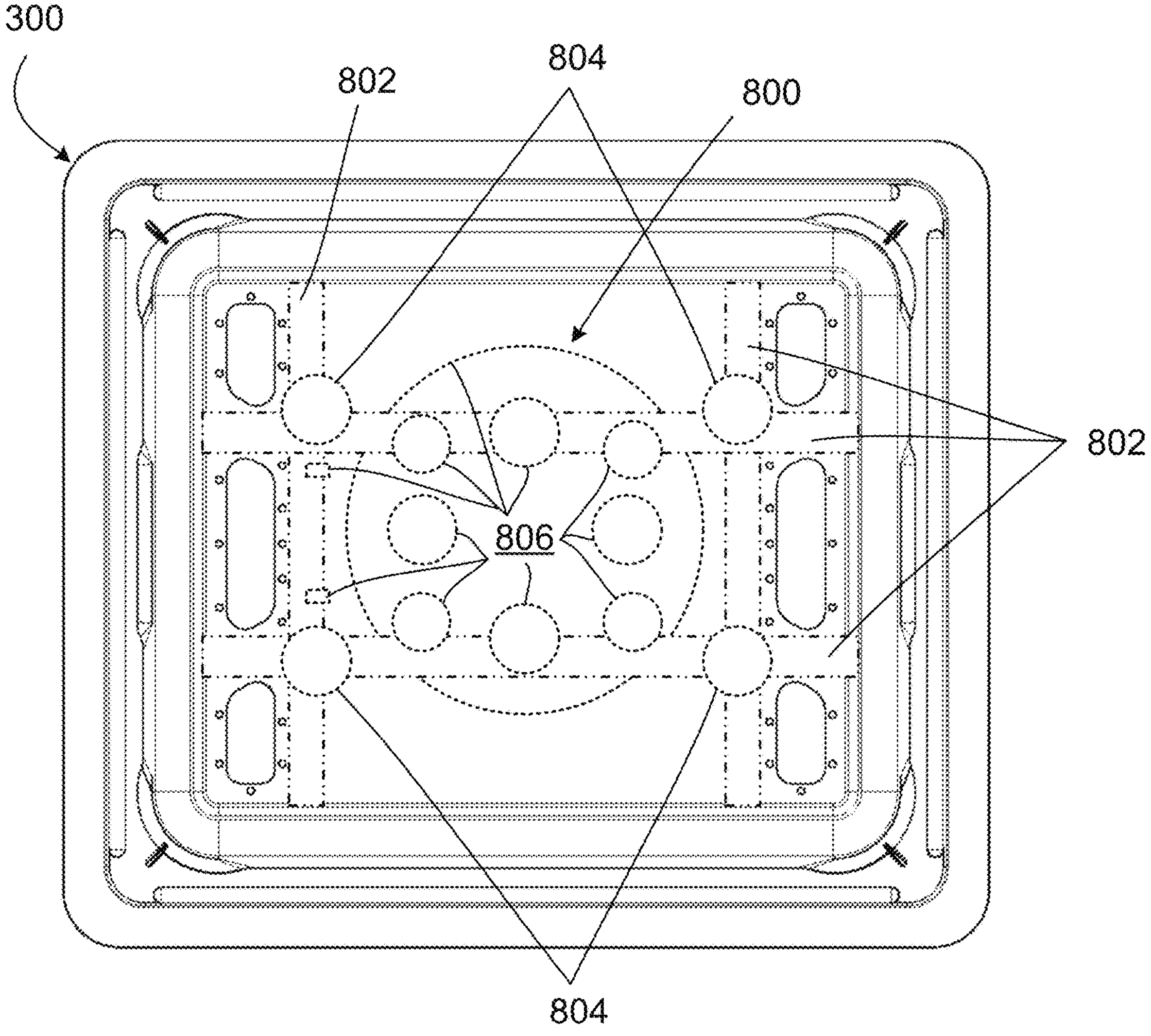
FIG. 8 is a schematic bottom view of an interference map displayed over the bottom wall 112 of the example tub of FIG. 3.

The layout of the apertures 114 on the bottom wall 112 of the example tub 300 provides sufficient open area through the bottom wall 112 to perform a sterilization and injection process through the apertures 114 without sacrificing structural rigidity of the tub 300. For example, the apertures 114 are aligned parallel with but slightly offset from the edges of the bottom wall 112 at the longitudinal ends 306 and 308. The location and position of the apertures 114 in the bottom wall 112 of the tub 300 can vary. However, the layout of the apertures 114 in the example tub 300 of FIG. 3 are positioned to avoid interference with other equipment that may be used during the formation, handling, and use of a packaging with the example tub 300. For example, the bottom wall 112 of the example tub 300 can be used as a mounting point or support point for rollers, suction pads, handling tools, or other machinery equipment during operations including manufacturing, filling, sterilizing, handling, transportation, and/or opening of a packaging that includes the example tub 300. FIG. 8 is a schematic bottom view of an interference map 800 displayed over the bottom wall 112 of the example tub 300 of FIG. 3. The interference map 800 indicates sections and areas on the bottom wall 112 that can be utilized by equipment in one or more of the above operations. The positioning of the apertures 114 in the bottom wall 112 avoids interference of the apertures 114 (and associated porous material inserts) with these equipment areas. For example, pattern 802 indicates an example roller interference, pattern 804 indicates an example suction pad interference, and pattern 806 indicates various example machine maker interferences. The apertures 114 do not overlap these patterns 802, 804, or 806, nor do the apertures 114 disrupt existing operational processes along these interference patterns.

In some implementations, the plurality of apertures 114 includes additional pinpoint apertures or dimples in the bottom wall 112. For example, the example tub 300 of FIGS. 3 and 5-7 include additional pinpoint apertures 310 adjacent to and spaced around the first plurality of apertures 302 and second plurality of apertures 304. These pinpoint dimples or apertures 310 provide mounting points or positioning points for the one or more inserts 104 of porous, semi-permeable material, such as during an overmolding operation of the tub 300 when the insert(s) 104 is overmolded with the tub 300. For example, the pinpoint apertures 310 can aid in the positioning of the inserts 104 during overmolding of the tub 300 plus inserts 104. In other examples, the pinpoint apertures 310 are carryover marks from holding pins that fix the inserts 104 in place during an injection molding process of the tub 300. These pinpoint apertures 310 of the example tub 300 of FIGS. 3 and 5-7 are optional, and may be arranged in other arrangements than that shown in FIGS. 3 and 5-7.

The apertures 114 can be molded into the tub 300 during the formation of the tub 300, cut out of the bottom wall 112 of the tub 300 after a main body of the tub 300 is formed, or otherwise formed in the tub 300. While the example tub 300 of FIGS. 3 and 5-7 is shown as having multiple apertures 114 in the bottom wall 112 of the tub 300, in some implementations, the sidewalls 116 can include apertures instead of or in addition to the apertures 114 in the bottom wall 112.

Figure 4:
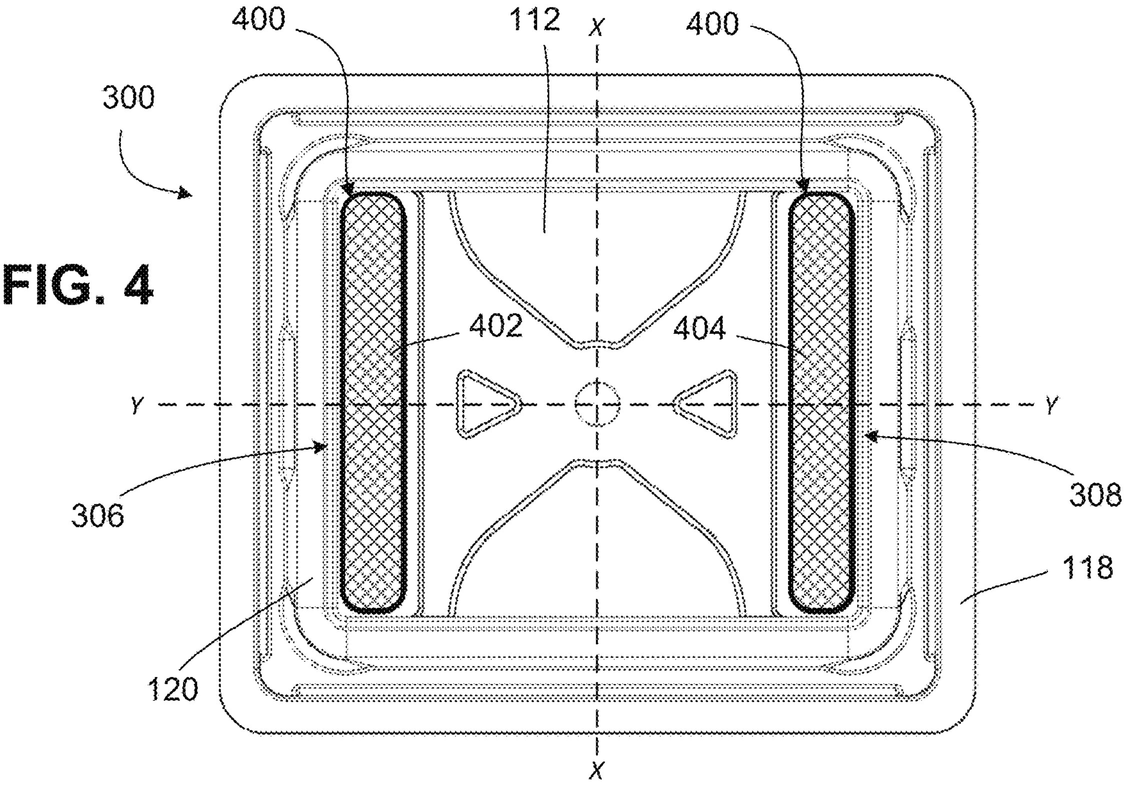
FIG. 4 is a schematic bottom view of the example tub of FIG. 3 including an insert of porous material.

FIG. 4 is also a schematic bottom view of the example tub 300 of FIG. 3, including inserts 400 of porous, semi-permeable material disposed over the apertures 114. The inserts 400 of porous (semi-permeable) material are the same as the insert 104 of porous material of the example packaging of FIG. 1, and can be used in the example packaging 100 of FIG. 1. The inserts 400 of porous material are sealed to the bottom wall 112 of the tub 300 over the apertures 114, and the porous material seals the apertures 114 from liquid penetration. The example inserts 400 of porous material of FIG. 4 are disposed over the apertures 114 in strips of the porous material (two shown). For example, a first strip 402 of porous material seals the first plurality of apertures 302 and a second strip 404 of porous material seals the second plurality of apertures 304. The example tub 300 of FIG. 4 includes two inserts 400, but a single insert or more than two inserts can be disposed over the apertures 114, for example, in instances with additional apertures or differently spaced apertures. In some implementations, the strips of porous material are incorporated into the molding formation of the tub 300 such that the strips are overmolded with the tub 300. Overmolding the strips of porous material can streamline the manufacture of the tub since the end product from the single molding operation includes a tub with porous material strips already sealed over the apertures.

In the example tub 300 of FIG. 4, the inserts 400 are shown as two separate inserts, where the first insert covers the first set of apertures on a first end of the tub 300 and the second insert covers the second set of apertures on a second end of the tub 300. In some implementations, the inserts 400 are a single sheet of porous, semi-permeable material that cover all of the apertures in the bottom wall 112 of the tub 300. The single sheet insert can cover the entire bottom wall 112 or only a portion of the bottom wall 112, as long as the single sheet covers the entirety of the apertures through the bottom wall 112. In some examples, the single sheet insert, or the multiple inserts 400, can be inserted in to a mould to be overmolded to the tub 300 during formation of the tub 300.

The porous, semi-permeable material can be made of a variety of gas-pervious and liquid-impervious materials, such as a medical grade fabric formed from HDPE fibers. For example, Tyvek can be used as the porous material. Tyvek is a synthetic fabric made from HDPE fibers and is resistant to water and bacterial invasion, and porous enough to allow gas penetration (such as disinfectant gas for sterilization). In some implementations, the inserts 400 of porous material include strips of Tyvek material, such as the first strip 402 being made of Tyvek and the second strip 404 being made of Tyvek.

Figure 9:
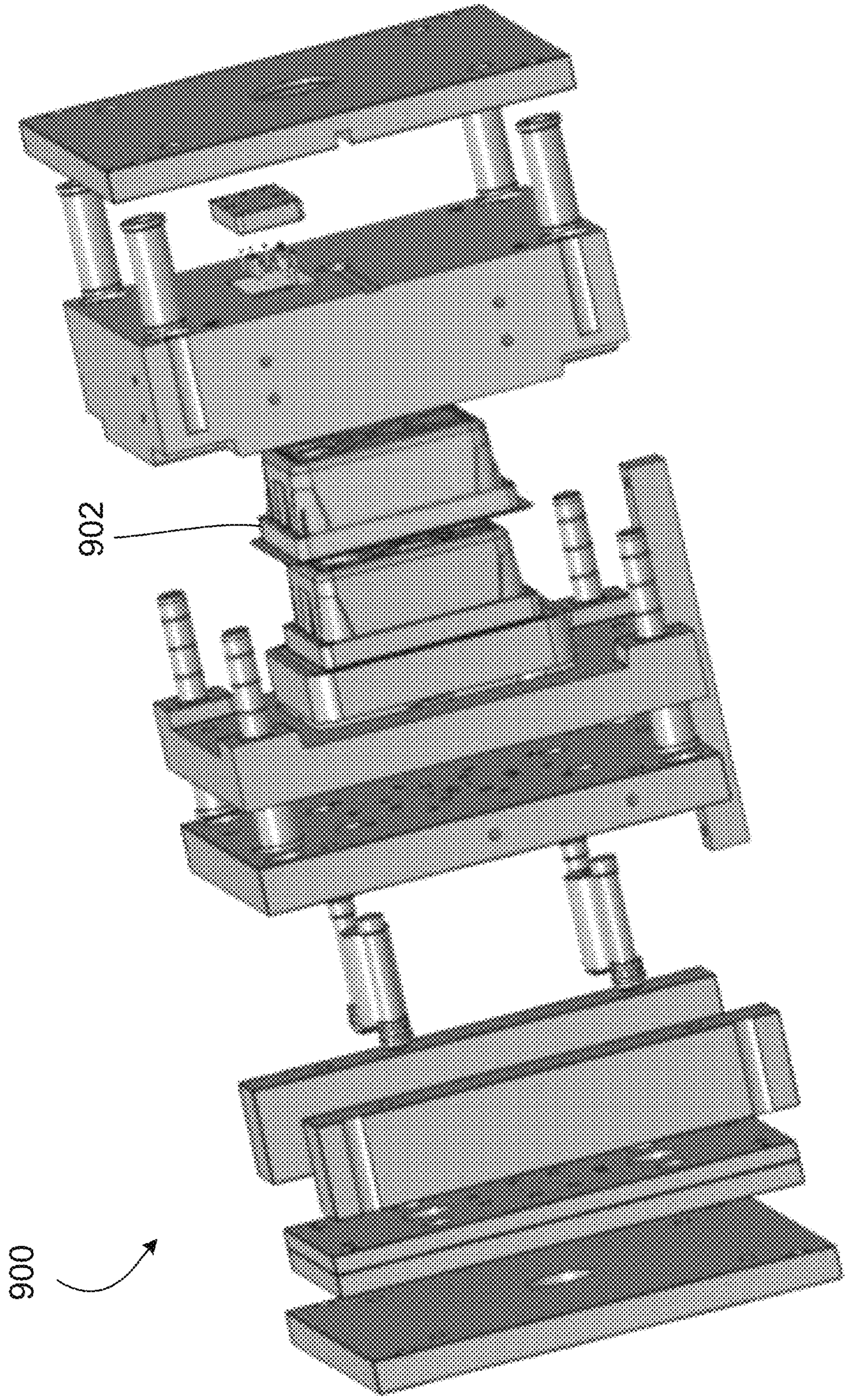
FIG. 9 is an exploded perspective view of an example tub and example molding assembly.

Fabrication of the example tub 300 can vary. As mentioned above, the example tub 300 can be thermoformed or injection molded using a mold, and the porous material insert(s) can be overmolded to the tub 300, heat sealed onto the tub 300, or otherwise coupled to the tub 300 and positioned over the apertures 114. FIG. 9 is an exploded perspective view of an example tub 902 in an example molding assembly 900. The example tub 902 is the same as the example tub 300 of FIG. 3. The example molding assembly 900 can be used to fabricate the example tub 902 including one or more overmolded inserts of porous material.

Figure 10:
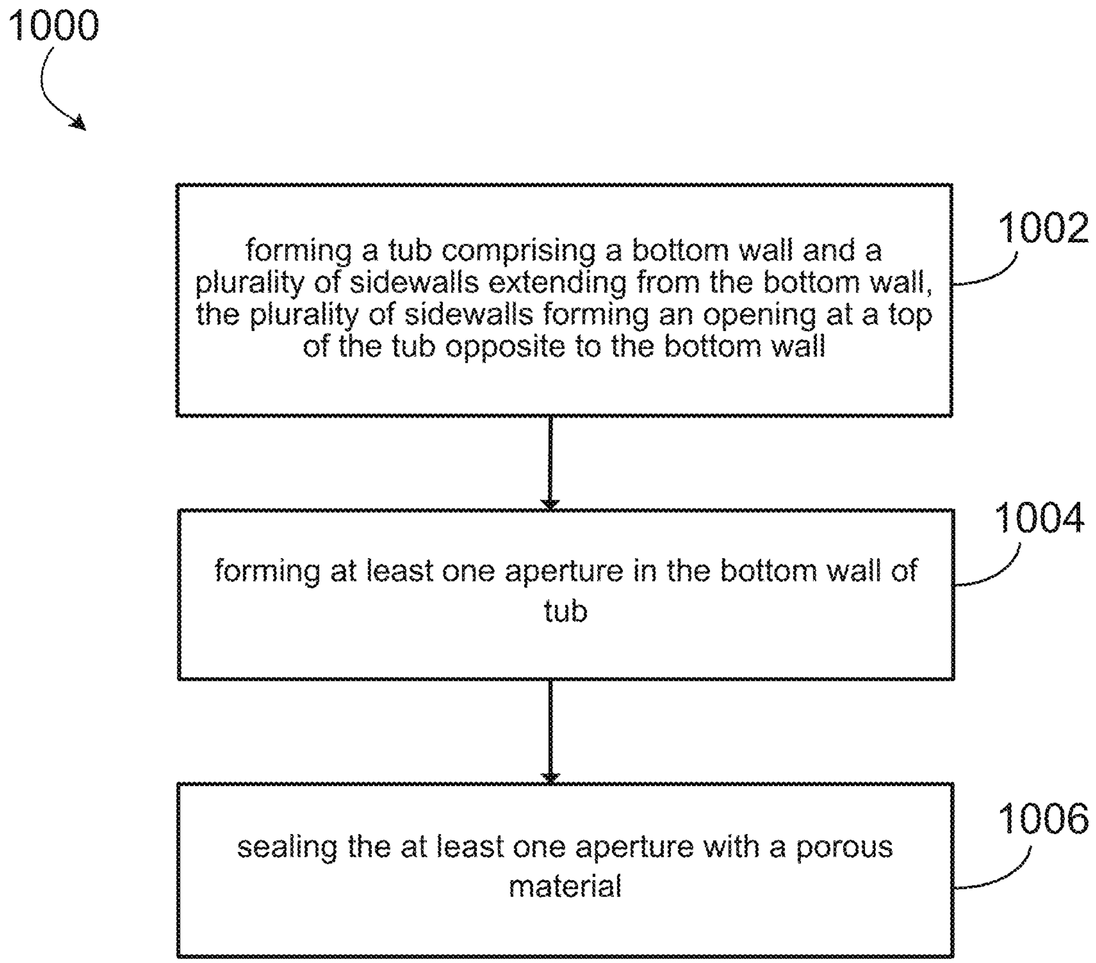
FIG. 10 is a flowchart of an example method for forming a tub or medical containers.

FIG. 10 is a flowchart of an example method 1000 for forming a tub for medical containers, such as the example tub 102 of FIGS. 1 and 2, the example tub 300 of FIGS. 3-8, or the example tub 902 of FIG. 9. At 1002, a tub is formed comprising a bottom wall and a plurality of sidewalls extending from the bottom wall. The plurality of sidewalls form an opening at a top of the tub opposite to the bottom wall. In some implementations, forming the tub comprises thermoforming or injection molding the tub. At 1004, at least one aperture is formed in the bottom wall of the tub. In some instances, forming the at least one aperture comprises molding the bottom wall of the tub to include the at least one aperture or cutting out the at least one aperture in the bottom wall of the tub. At 1006, the at least one aperture is sealed with a porous material. In some implementations, sealing the at least one aperture with the porous material comprises overmolding the porous material with the tub or heat sealing the porous material to the tub. In certain instances, the porous material includes Tyvek, and the at least one aperture is sealed with Tyvek.

Figure 11:
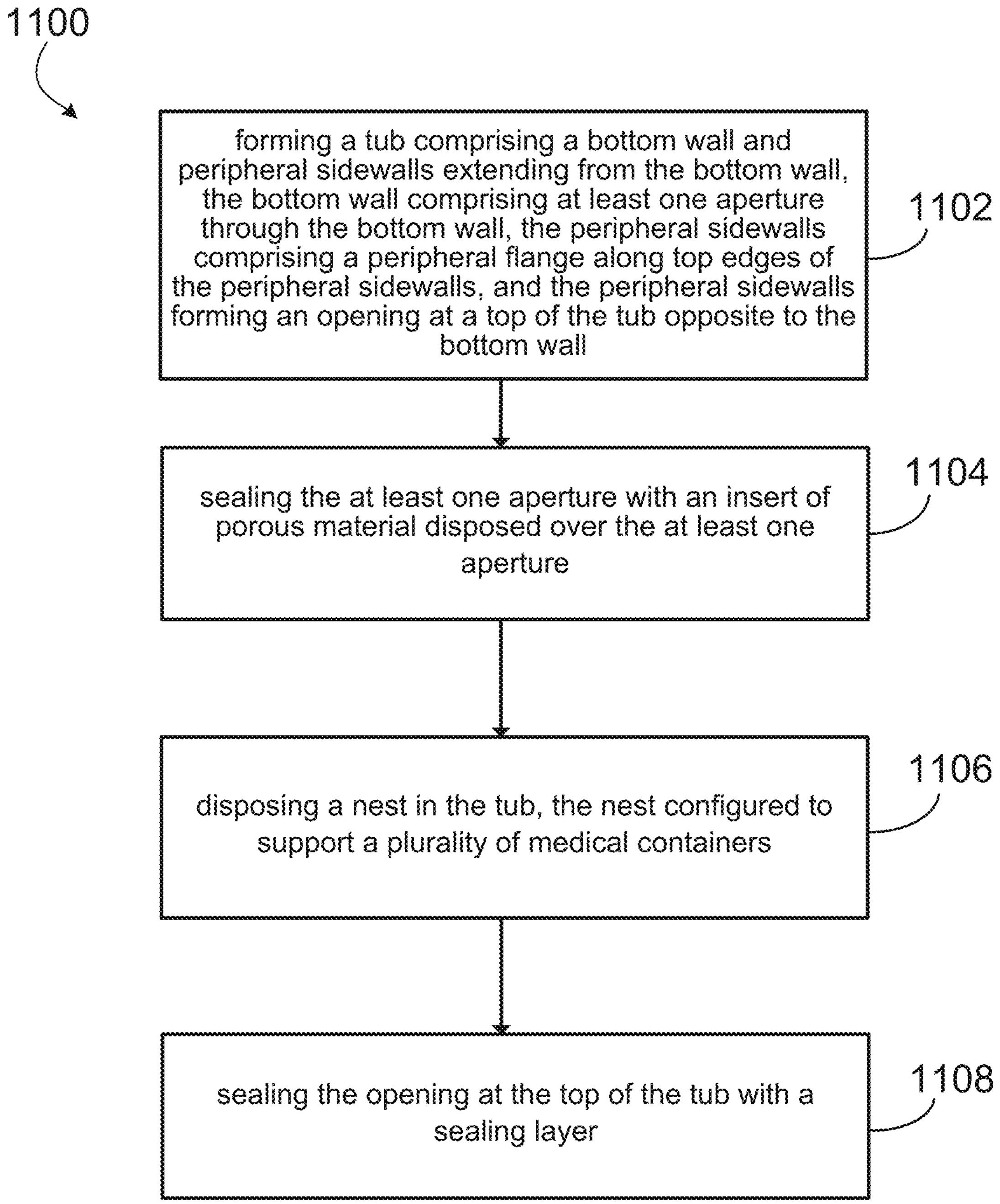
FIG. 11 is a flowchart of an example method for forming a sterilized packaging for medical containers.

FIG. 11 is a flowchart of an example method 1100 for forming a sterilized packaging for medical containers, such as the example packaging 100 of FIGS. 1 and 2. At 1102, a tub is formed comprising a bottom wall and peripheral sidewalls extending from the bottom wall. The bottom wall comprises at least one aperture through the bottom wall, the peripheral sidewalls comprise a peripheral flange along top edges of the peripheral sidewalls, and the peripheral sidewalls form an opening at a top of the tub opposite to the bottom wall. In some instances, forming the tub includes thermoforming or injection molding the tub. At 1104, the at least one aperture is sealed with an insert of porous material disposed over the at least one aperture. Sealing the at least one aperture with the insert of porous material can include overmolding the porous material with the tub or heat sealing the porous material to the tub. At 1106, a nest is disposed in the tub, the nest being configured to support a plurality of medical containers. At 1108, the opening is sealed at the top of the tub with a sealing layer. In certain implementations, sealing the opening at the top of the tub with the sealing layer comprises adhering the sealing layer to the peripheral flange with an adhesive, and optionally, in a continuous, non-linear pattern along the peripheral flange, such as in a sinusoidal pattern. In some examples, the method 1100 includes injecting disinfectant through the porous material and into an interior of the tub, where the disinfectant sterilizes the plurality of medical containers. In certain examples, the method 1100 also includes removing the sealing layer from the tub, such as by suction roller cutting, grating, or manual stripping of the sealing layer from the tub. The removal of the sealing layer can occur in a sterile environment, for example, to maintain that the packaging is sterile.

A number of implementations have been described. Nevertheless, it will be understood that various modifications may be made without departing from the spirit and scope of the disclosure.

What is claimed is:

1. A tub for storing medical containers, the tub comprising:

a bottom wall comprising a plurality of apertures through the bottom wall, the plurality of apertures comprising a first plurality of apertures disposed at a first longitudinal end of the bottom wall and a second plurality of apertures at a second longitudinal end of the bottom wall opposite to the first longitudinal end, wherein a surface of the bottom wall extending between the first plurality of apertures and the second plurality of apertures is unapertured, wherein the unapertured surface of the bottom wall extends a majority of the longitudinal length of the bottom wall between the first longitudinal end and the second longitudinal end; and a plurality of sidewalls extending from the bottom wall, the plurality of sidewalls forming an opening at a top of the tub opposite to the bottom wall, wherein the apertures of the first plurality of apertures are linearly aligned in parallel to the sidewall at the first longitudinal end of the bottom wall, and the apertures of the second plurality of apertures are linearly aligned in parallel to the sidewall at the second longitudinal end of the bottom wall.

2. The tub of claim 1 wherein the bottom wall is substantially rectangular, and the plurality of sidewalls comprises a first set of sidewalls along longitudinal edges of the bottom wall and a second set of sidewalls along lateral edges of the bottom wall.

3. The tub of claim 1, wherein the opening comprises a peripheral flange along top edges of the plurality of sidewalls, the peripheral flange being continuous along the plurality of sidewalls.

4. The tub of claim 1, wherein the plurality of apertures are disposed in a symmetrical pattern across a lateral centerline of the bottom wall.

5. The tub of claim 1, wherein the first plurality of apertures comprises a first set of three apertures aligned adjacent to the first longitudinal end of the bottom wall, and the second plurality of apertures comprises a second set of three apertures aligned adjacent to the second longitudinal end of the bottom wall.

6. The tub of claim 1, further comprising a porous fiber material disposed over the plurality of apertures of the bottom wall of the tub.

7. The tub of claim 6, wherein the porous fiber material is disposed over the plurality of apertures in strips of porous material.

8. The tub of claim 7, wherein a first strip of the porous material is disposed over the first plurality of the apertures, and a second strip of the porous material is disposed over the second plurality of the apertures.

9. The tub of claim 6, wherein the porous fiber material comprises Tyvek.

10. The tub of claim 1, wherein the tub is laterally symmetrical and longitudinally symmetrical.

11. The tub of claim 1, wherein the first plurality of apertures comprises a first aperture having a first size and a second aperture having a second size smaller than the first size.

12. The tub of claim 11, wherein the second plurality of apertures comprises a third aperture having the first size and a fourth aperture having the second size.

13. The tub of claim 11, wherein the first plurality of apertures comprises a third aperture having the second size, and the first plurality of apertures are disposed in a linear pattern with the first aperture disposed between the second aperture and the third aperture.

14. The tub of claim 1, wherein each aperture of the plurality of apertures comprises an elongate shape.

15. The tub of claim 1, wherein the first plurality of apertures comprises three or fewer apertures, and the second plurality of apertures comprises three or fewer apertures.

16. A tub for storing medical containers, the tub comprising:

a bottom wall comprising a plurality of apertures through the bottom wall, the plurality of apertures comprising a first plurality of apertures disposed at a first longitudinal end of the bottom wall and a second plurality of apertures at a second longitudinal end of the bottom wall opposite to the first longitudinal end, wherein the first plurality of apertures comprises a first aperture having a first size, a second aperture having a second size smaller than the first size, and a third aperture having the second size, the second plurality of apertures comprises a fourth aperture having the first size, a fifth aperture having the second size, and a sixth aperture having the first size, the first plurality of apertures are disposed in a linear pattern with the first aperture disposed between the second aperture and the third aperture, the plurality of apertures are disposed in a symmetrical pattern across a lateral centerline of the bottom wall, and a surface of the bottom wall extending between the first plurality of apertures and the second plurality of apertures is unapertured; and a plurality of sidewalls extending from the bottom wall, the plurality of sidewalls forming an opening at a top of the tub opposite to the bottom wall.

17. The tub of claim 16, wherein the unapertured surface of the bottom wall extends a majority of the longitudinal length of the bottom wall between the first longitudinal end and the second longitudinal end.

18. The tub of claim 17, wherein the apertures of the first plurality of apertures are linearly aligned in parallel to the sidewall at the first longitudinal end of the bottom wall, and the apertures of the second plurality of apertures are linearly aligned in parallel to the sidewall at the second longitudinal end of the bottom wall.

* * * * *